United States Patent [19]

Proudfoot et al.

[11] Patent Number: 5,919,779
[45] Date of Patent: Jul. 6, 1999

[54] 5,6-HETEROARYL-DIPYRIDO(2,3-B:3', 2'-F) AZEPINES AND THEIR USE IN THE PREVENTION OR TREATMENT OF HIV INFECTION

[75] Inventors: John R. Proudfoot, Newtown; Karl D. Hargrave, Brookfield; Suresh Kapadia, Danbury, all of Conn.

[73] Assignee: Boehringer Ingelheim Pharmaceuticals, Inc., Ridgefield, Conn.

[21] Appl. No.: 09/132,526

[22] Filed: Aug. 11, 1998

Related U.S. Application Data

[60] Provisional application No. 60/055,189, Aug. 11, 1997.
[51] Int. Cl.$^6$ .................. A61K 31/55; C07D 487/00; C07D 498/00; C07D 513/00
[52] U.S. Cl. ............................. 514/215; 540/578
[58] Field of Search ............................. 540/578; 514/215

[56] References Cited

U.S. PATENT DOCUMENTS 5,366,972  11/1994  Hargrave et al. .................. 514/229

OTHER PUBLICATIONS

Terett et al. (Bioorganic & Medicinal Chemistry Letters, vol. 2, No. 12, pp. 1745–1750, 1992).
Proudfoot et al. (J. Med. Chem. 1995, 38, 4830–4838).
Hargrave et al. (J. Med. Chem. 1991, 34, 2231–2241).

*Primary Examiner*—Richard L. Raymond
*Assistant Examiner*—Bruck Kifle
*Attorney, Agent, or Firm*—Robert P. Raymond; Alan R. Stempel; Mary Ellen Devlin

[57] ABSTRACT

"There are disclosed compounds of the formula I, II or III wherein A and D are carbon or nitrogen and B is oxygen, sulfur or nitrogen which are useful in the prevention or treatment of HIV infection."

7 Claims, No Drawings

5,6-HETEROARYL-DIPYRIDO(2,3-B:3', 2'-F) AZEPINES AND THEIR USE IN THE PREVENTION OR TREATMENT OF HIV INFECTION

CROSS-REFERENCE TO RELATED APPLICATIONS

The benefit of prior provisional application Ser. No. 60/055,189, filed on Aug. 11, 1997, is hereby claimed.

FIELD OF THE INVENTION

The invention relates to novel 5,6-heteroaryldipyrido[2,3-b:3',2'-f]azepines and pharmaceutically acceptable salts thereof, methods for preparing these compounds, the use of these compounds either alone or in combination with other anti-virals, immunomodulators, antibiotics, anti-infectives, or vaccines in the prevention or treatment of HIV infection, and to pharmaceutical compositions containing these compounds.

BACKGROUND OF THE INVENTION

The human disease, Acquired Immune Deficiency Syndrome (AIDS), is caused by the Human Immunodeficiency Virus (HIV), particularly the strain known as HIV-1.

Like other viruses, HIV-1 cannot replicate without commandeering the biosynthetic apparatus of the host cell it infects. It causes this apparatus to produce the structural proteins which make up the viral progeny. These proteins are coded for by the genetic material contained within the infecting virus particle, or virion. Being a retrovirus, however, the genetic material of HIV is RNA, not DNA as in the host cell's genome. Accordingly, the viral RNA must first be converted into DNA, and then integrated into the host cell's genome, in order for the host cell to produce the required viral proteins. The conversion of the RNA to DNA is accomplished by the enzyme reverse transcriptase (RT), which along with the RNA is a component of the infecting virion. Reverse transcriptase has three known enzymatic functions; it acts as an RNA-dependent DNA polymerase, as a ribonuclease, and as a DNA-dependent DNA polymerase. Acting first as an RNA-dependent DNA polymerase, RT makes a single-stranded DNA copy of the viral RNA. Acting as a ribonuclease, RT frees the DNA just produced from the original viral RNA and destroys the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds which inhibit the enzymatic functions of HIV-1 reverse transcriptase will inhibit replication of HIV-1 in infected cells. Such compounds are useful in the prevention or treatment of HIV-1 infection in human subjects as demonstrated by the known RT inhibitors 3'-azido-3'-deoxythymidine (AZT), 2',3'-dideoxyinosine (ddI), and 2',3'-dideoxycytidine (ddC), and D4T the only drugs thus far approved for use in the treatment of AIDS and AIDS-related Complex (ARC).

As with any anti-viral therapy, use of RT inhibitors in the treatment of AIDS eventually leads to virus which is less sensitive to the given drug. Resistance (reduced sensitivity) to these drugs is the result of mutations which occur in the reverse transcriptase segment of the pol gene. The compounds of the present invention are highly potent against not only the wild-type (non-mutated) virus RT enzyme, but are also effective against the reverse transcriptase of many mutant viruses which have been observed in patients who have been treated with RT inhibitors.

Specifically, the compounds of the present invention are effective in inhibiting the Y181C mutant [in which the tyrosine (Y) at codon 181 has been mutated to a cysteine (C) residue] which has been the most commonly observed mutant in clinical studies following therapy with many non-nucleoside reverse transcriptase inhibitors. The compounds are also effective against other observed mutant enzymes which contain a single point mutation such as K103N, V106A, G190A, Y188C, or P236L.

PRIOR ART

K. D. Hargrave, J. R. Proudfoot, J. Adams, K. G. Grozinger, G. Schmidt, W. Engel, G. Trummlitz, and W. Eberlein, U.S. appl. 740,828 (1991); Karl D. Hargrave, John R. Proudfoot, Karl G. Grozinger, Ernest Cullen, Suresh R. Kapadia, Usha R. Patel, Victor U. Fuchs, Scott C. Mauldin, Jana Vitous, Mark L. Behnke, Janice M. Klunder, Kollol Pal, Jerry W. Skiles, Daniel W. McNeil, Janice M. Rose, Grace Chow, Mark T. Skoog, Joe C. Wu, Günther Schmidt, Wolfhard W. Engel, Wolfgang G. Eberlein, Tracy D. Saboe, Scot J. Campbell, Alan S. Rosenthal, and Julian Adams, "Novel Non-Nucleoside Inhibitors of HIV-1 Reverse Transcriptase. 1. Tricyclic Pyridobenzo- and Dipyridodiazepinones", *J. Med. Chem.*, 34, 2231 (1991).

N. K. Terrett, D. Bojanic, J. R. Merson, and P. T. Stephenson, "Imidazo[2',3':6,5]dipyrido[3,2-b:2', 3'-e][1,4]diazepines: Non-Nucleoside HIV-1 Reverse Transcriptase Inhibitors with Greater Enzyme Affinity than Nevirapine", *Bioorg. Med. Chem. Lett.*, 2, 1745 (1992).

John R. Proudfoot*, Karl D. Hargrave, Suresh R. Kapadia, Usha R. Patel, Karl G. Grozinger, Daniel W. McNeil, Ernest Cullen, Mario Cardozo, Liang Tong, Terence A. Kelly, Janice Rose, Eva David, Scott C. Mauldin, Victor U. Fuchs, Jana Vitous, MaryAnn Hoermann, Janice M. Klunder, Palayakotai Raghavan, Jerry W. Skiles, Philip Mui, Douglas D. Richman, John L. Sullivan, Cheng-Kon Shih, Peter Grob, and Julian Adams. "Novel Non-Nucleoside Inhibitors of HIV-1 Reverse Transcriptase. 4. 2-Substituted Dipyridodiazepinones are Potent Inhibitors of both Wild Type and Cysteine-181 HIV-1 Reverse Transcriptase Enzymes." *J. Med. Chem.* 38, 4830, (1995).

SUMMARY OF THE INVENTION

A first aspect of the invention comprises novel dipyrido[2,3-b:3',2'-f]azepines. These possess inhibitory activity against both wild-type and mutant HIV-1 RT. A second aspect of the invention comprises methods for making these novel compounds. A third aspect of the invention is a method for preventing or treating HIV-1 infection which comprises administering, to a human being exposed to or infected by HIV-1, a prophylactically or therapeutically effective amount of one of the above-mentioned novel compounds, either alone or in combination with other anti-viral agents. A final aspect of the invention comprises pharmaceutical compositions suitable for the prevention or treatment of HIV-1 infection comprising the above-mentioned compounds.

DESCRIPTION OF THE INVENTION

In one of its composition of matter aspects, the invention comprises dipyrido[2,3-b:3', 2'-f]azepines of formula I, formula II and formula III

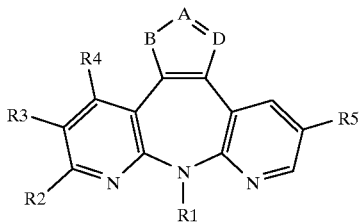

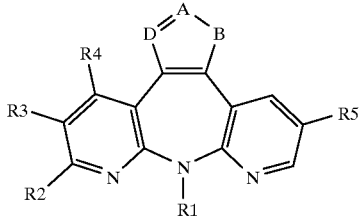

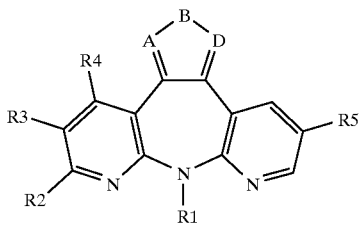

wherein:
in formula I, formula II and formula III, A and D are independently carbon (unsubstituted or optionally substituted with methyl, ethyl, isopropyl, vinyl, isopropenyl, ethynyl, halogen, nitro, cyano, amino, methylamino, dimethylamino, hydroxy, methoxy, mercapto or methylthio) or nitrogen, and B is sulfur, oxygen, or nitrogen (unsubstituted or optionally substituted with methyl, ethyl, isopropyl, hydroxy or methoxy); and;

$R_1$ is a hydrogen atom, alkyl of 1 to 4 carbon atoms, fluoroalkyl of 1 to 4 carbon atoms and 1 to 3 fluorine atoms, cycloalkyl of 3 to 6 carbon atoms, oxetanyl, thietanyl, tetrahydrofuranyl, tetrahydrothienyl, tetrahydropyranyl, tetrahydrothiopyranyl, alkenylmethyl or alkynylmethyl of 3 to 4 carbon atoms, alkyloxyalkyl or alkylthioalkyl of 2 to 3 carbon atoms, alkanoyl or alkyl(thiocarbonyl) of 2 to 5 carbon atoms, or cyanoalkyl of 2 to 3 carbon atoms;

and, $R_2$ is a hydrogen atom, alkyl of 1 to 6 carbon atoms, cycloalkyl of 3 to 6 carbon atoms, alkenyl or alkynyl of 2 to 6 carbon atoms, trihalomethyl, hydroxyalkyl of 1 to 6 carbon atoms, alkyloxy or alkylthio of 2 to 6 carbon atoms, alkyloxyalkyl or alkylthioalkyl of 2 to 6 carbon atoms, pyrrolidinyl, pyrrolinyl, piperidinyl, mono- or di-alkylamino wherein each alkyl moiety contains 1 to 3 carbon atoms, halogen, cyano, nitro, or carboxyl, aryl (wherein aryl is phenyl, pyridinyl, thienyl, furanyl, pyrrolyl, imidazolyl, pyrazolyl, oxazolyl, isoxazolyl, thiazolyl or isothiazolyl) which is either unsubstituted or substituted by hydroxyl, amino, halogen, alkyl or alkyloxy of 1 to 3 carbon atoms, and, $R_3$ is a hydrogen atom, methyl or halogen;

$R_4$ is a hydrogen atom, methyl, ethyl or halogen;

$R_5$ is a hydrogen atom, hydroxy, amino, hydroxymethyl or aminomethyl.

A subgeneric aspect of the invention comprises compounds of formula I, formula II and formula III wherein:
in formula I, formula II and formula III, A and D are independently carbon (unsubstituted or optionally substituted with methyl, cyano or halogen) or nitrogen and B is sulfur or oxygen or nitrogen (unsubstituted or optionally substituted with methyl);

and, $R_1$ is alkyl of 1 to 3 carbon atoms or cycloalkyl of 3 to 4 carbon atoms;

$R_2$ is a hydrogen atom, methyl, trihalomethyl, methoxy, pyrrolidinyl, pyrrolinyl, piperidinyl, dimethylamino, halogen, cyano, nitro or aryl (wherein aryl is phenyl, pyridinyl, thienyl, furanyl, pyrrolyl, imidazolyl, pyrazolyl, oxazolyl, isoxazolyl, thiazolyl or isothiazolyl) which is either unsubstituted or substituted by methyl, methoxy, hydroxyl, amino, or halogen;

$R_3$ is a hydrogen atom, methyl, chloro or bromo;

$R_4$ is hydrogen or methyl;

and, $R_5$ is a hydrogen atom.

A particular subgeneric aspect of the invention comprises compounds of formula I, formula II and formula III wherein:
in formula I, formula II and formula III, A and D are independently carbon or nitrogen, and B is sulfur, oxygen or nitrogen;

and, $R_1$ is ethyl or cyclopropyl;

$R_2$ is hydrogen, chloro, or pyrazolyl;

$R_3$, and $R_5$ are hydrogen;

$R_4$ is hydrogen or methyl.

Preferred compounds of formula I, formula II and formula III are:

11-Ethyl-thienyl[2',3':6,5]dipyrido[2,3-b:3',2'-f]azepine;

11-Ethyl-thienyl[3',4':6,5]dipyrido[2,3-b:3',2'-f]azepine;

2-Chloro-11-ethyl-thienyl[2',3':6,5]dipyrido[2,3-b: 3',2'-f]azepine;

2-(4-Pyrazolyl)-11-ethyl-thienyl[2',3': 6,5]dipyrido[2,3-b:3',2'-f]azepine;

11-Ethyl-thiazolyl[4',5':6,5]dipyrido[3,2-b:2',3'*f*]azepine;

8-Ethyl-oxazolo[4',5':6,5]dipyrido[2,3-b:3',2'-f]azepine;

8-Ethyl-(1, 2, 3)thiadiazolo[4',5':6,5]dipyrido[2,3-b:3',2'-f]azepine;

6-Bromo-8-ethyl-(1, 2, 3)thiadiazolo[4',5': 6,5]dipyrido[2,3-b:3',2'-f]azepine;

6-Ethynyl-8-ethyl-(1, 2, 3)thiadiazolo[4',5':6,5]dipyrido[2,3-b:3',2'-f]azepine;

6-Phenylethyl-8-ethyl-(1, 2, 3)thiadiazolo[4',5': 6,5]dipyrido[2,3-b:3',2'-f]azepine;

11-Ethyl-oxazolyl[4',5':6,5]dipyrido[3,2-b:2',3'-e]azepine; and,

11-Ethyl-thiadiazolyl[4',5':6,5]dipyrido[3,2-b:2',3'-e]azepine.

The compounds of formula I, formula II and formula III, and their salts, can be prepared by known methods or obvious modifications thereof. Methods A–C, described below, are illustrative of the methods for preparing the compounds.

Method A

Compounds of formula I, formula II and formula III above wherein A, B, and D, and $R_1$ through $R_5$ are as defined above, may be obtained by cyclizing compounds of formula IV, V and VI respectively

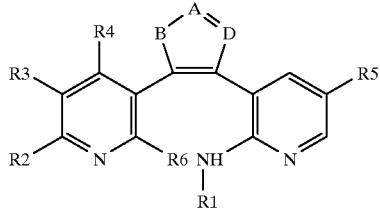
IV

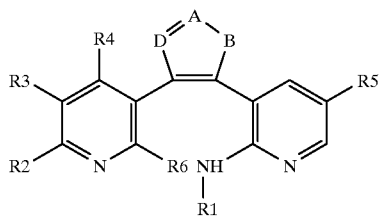
V

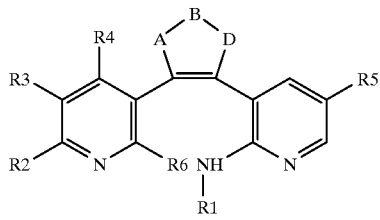
VI wherein A, B and D, and $R_1$ through $R_5$ are as defined above, and $R_6$ is a fluoro or chloro substituent. These reactions are generally carried out under an inert atmosphere of argon or nitrogen, and in inert solvents such as 1,4-dioxane or tetrahydrofuran and the like, at temperatures generally between room temperature and the boiling point of the solvent in the presence of a base such as sodium hydride or sodium bistrimethylsilylamide.

Compounds of formula IV, formula V and formula VI above wherein A, B, and D, and $R_1$ through $R_6$ are as defined above, may be obtained from compounds of formula VII, formula VIII and formula IX

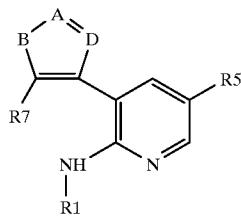
VII

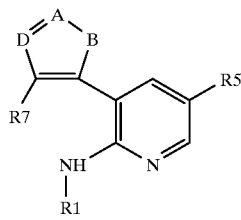
VIII

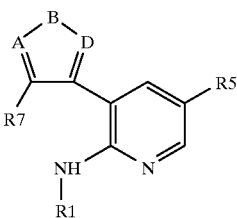
IX wherein A, B and D, and $R_1$ and $R_5$ are as defined above, and $R_7$ is bromo or iodo, by reaction with a compound of formula X

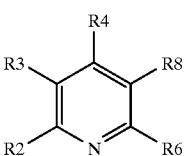
X wherein $R_8$ is tributylstannyl or trimethylstannyl and $R_2$, $R_3$, $R_4$ and $R_6$ are as defined above, in an inert solvent such as tetrahydrofuran, dioxane, dimethylformamide or N-methylpyrrolidinone at a temperature between room temperature and the boiling point of the solvent in the presence of a catalyst such as $Pd(Ph_3P)_2Cl_2$ or $Pd(Ph_3P)_4$ or $Pd(Ph_3As)_4$.

Compounds of formula VII, formula VIII and formula IX may be obtained from compounds of formula XI, formula XII and formula XIII

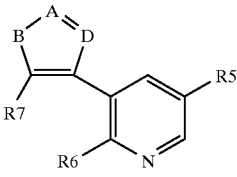
XI

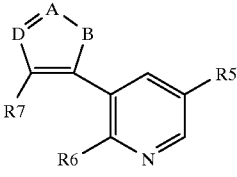
XII

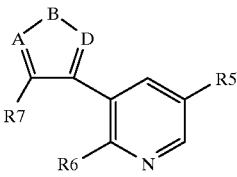
XIII wherein A, B and D, and $R_5$, $R_6$ and $R_7$ are as defined above, by reaction with a compound of formula XIV, $$R_1\text{—}NH_2 \qquad \text{XIV}$$

wherein $R_1$ is defined above. These reactions are generally carried out in an inert solvent such as 1,4-dioxane or tetrahydrofuran, and the like, generally between room temperature and the boiling point of the solvent. In cases where the boiling point of XIV is lower than the boiling point of the solvent it may be advantageous to use a sealed reaction vessel.

Compounds of formula XI, formula XII and formula XIII may be obtained from compounds of formula XV, formula XVI and formula XVII

XV

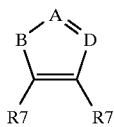

XVI

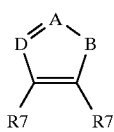

XVII

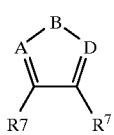

wherein A, B and D, and $R_7$ are as defined above by reaction with a compound of formula XVIII

XVIII

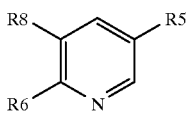

wherein $R_5$, $R_6$ and $R_8$ are as defined above, by reaction in an inert solvent such as tetrahydrofuran, dioxane, dimethylformamide or N-methylpyrrolininone at a temperature between room temperature and the boiling point of the solvent in the presence of a catalyst such as $Pd(Ph_3P)_2Cl_2$ or $Pd(Ph_3P)_4$ or $Pd(Ph_3As)_4$.

Compounds of formula X and formula XVIII, may be obtained from compounds of formula XIX or formula XX by lithiation followed by reaction with the appropriate trialkyltinhalide following known literature methods.

XIX

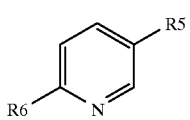

XX

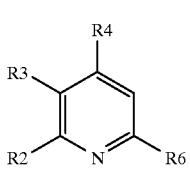

Method B

Compounds of formula IV, formula V and formula VI above wherein A, B, and D, and $R_2$ through $R_5$ are defined above, may be obtained from compounds of formula XXI, formula XXII and formula XXIII

XXI

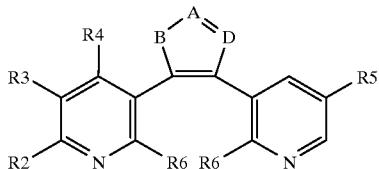

XXII

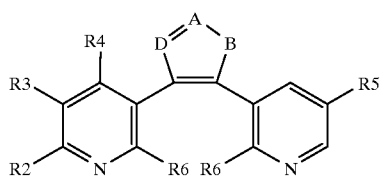

XXIII

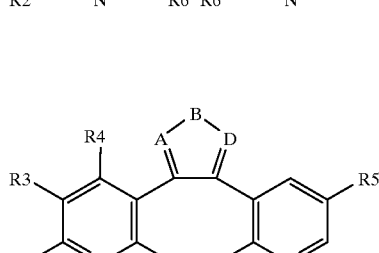

wherein A, B and D, and $R_2$ through $R_6$ are as defined above by reaction with a compound of formula XIV

XIV $R_1—NH_2$ wherein $R_1$ is defined above. These reactions are generally carried out in an inert solvent such as 1,4-dioxane or tetrahydrofuran and the like generally between room temperature and the boiling point of the solvent. In cases where the boiling point of XIV is lower than the boiling point of the solvent it may be advantageous to carry out the reaction in a closed vessel.

Compounds of formula XXI, formula XXII and formula XXIII above wherein A, B, and D, and $R_1$ through $R_4$ are as defined above, may be obtained from compounds of formula XXIV

XXIV

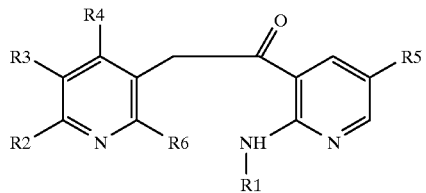

Wherein $R_2$ through $R_6$ are as defined above by standard methods of 5-membered heterocyclic ring formation.

It will be obvious to those skilled in the art that in some instances the reactions described in Methods A and B cannot be effected in the presence of reactive intermediates incompatible with the reaction conditions. In such cases, the reactive substituent must first be derivatized via known per se methods to contain a suitable protective group, which can then be subsequently removed.

Biological Properties

The above described compounds of formula I, formula II and formula III possess inhibitory activity against HIV-1 reverse transcriptase. When administered in suitable dosage forms, they are useful in the prevention or treatment of AIDS, ARC and related disorders associated with HIV-1 infection. Another aspect of the invention, therefore, is a method for preventing or treating HIV-1 infection which comprises administering to a human being, exposed to or infected by HIV-1, a prophylactically or therapeutically effective amount of a novel compound of formula I, formula II or formula III, as described above.

The compounds of formula I, formula II and formula III may be administered in single or divided doses by the oral, parenteral or topical routes. A suitable oral dosage for a compound of formula I, formula II and formula III would be in the range of about 0.5 mg to 1 g per day. A preferred oral dosage for a compound of formula I, formula II and formula III would be in the range of about 100 mg to 800 mg per day. In parenteral formulations, a suitable dosage unit may contain from 0.1 to 250 mg of said compounds, preferably 1 mg to 200 mg, whereas for topical administration, formulations containing 0.01 to 1% active ingredient are preferred. It should be understood, however, that the dosage administration from patient to patient will vary and the dosage for any particular patient will depend upon the clinician's judgment, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I, formula II and formula III can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application, and may contain in addition to the compounds of this invention suitable buffers, tonicity adjusters, microbial preservatives, antioxidants, and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenyl-ethyl alcohol.

Additionally, the compounds provided by the invention can be administered by suppository.

As stated before, the compounds provided by the invention inhibit the enzymatic activity of HIV-1 RT. Based upon testing of these compounds, as described below, it is known that they inhibit the RNA-dependent DNA polymerase activity of HIV-1 RT. It is known (data not shown) that they also inhibit the DNA-dependent DNA polymerase activity of HIV-1 RT.

Utilizing the Reverse Transcriptase (RT) Assay described below, compounds can be tested for their ability to inhibit the RNA-dependent DNA polymerase activity of HIV-1 RT. Certain specific compounds described in the Examples which appear below, were so tested. The results of this testing appear in Table I, below.

REVERSE TRANSCRIPTASE (RT) ASSAYS

Assay Theory:

Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay, which has been previously described (2), and is based upon the observation that reverse transcriptase is able to use a synthetic template [poly r(C) primed with oligo d(G)] to transcribe a radio-labelled, acid-precipitable DNA strand utilizing $^3$H-dGTP as a substrate. The assay described below utilizes the wild type (WT) enzyme, which is the predominant form of the enzyme observed in patients infected with HIV-1. Utilization of the mutant RT enzyme (Y181C, prepared by site-directed mutagenesis in which the tyrosine residue at codon 181 has been replaced by a cysteine residue), and analogous assay conditions, allows compounds to be evaluated for their effectiveness at inhibiting this mutant enzyme.

Materials:

a) Preparation of the wild type enzyme

Reverse transcriptase enzyme from the LAV strain of Human Immunodeficiency Virus (HIV-1) (1) was isolated from the bacterial strain JM109 (3) expressing the DNA clone pBRTprt1+ (2) which is under the control of the lac promotor in the expression vector pIBI21 (4). An overnight culture grown in 2XYT medium (37° C., 225 rpm) (5) supplemented with 100 μg/mL ampicillin for positive selection is inoculated at a 1:40 dilution into M9 medium supplemented with 10 μg/mL thiamine, 0.5% casamino acids, and 50 μg/mL ampicillin (5). The culture is incubated (37° C., 225 rpm) until it reaches an OD540 of 0.3–0.4. At that time the repressor inhibitor IPTG (isopropyl β-D-thiogalactopyranoside) is added to 0.5 mM, and the mixture is incubated for 2 additional hours. Bacteria are pelleted, resuspended in a 50 mM Tris, 0.6 mM EDTA, 0.375M NaCl buffer, and digested by the addition of lysozyme (1 mg/mL) for 30 minutes on ice. The cells are lysed by the addition of 0.2% NP-40, and brought to 1M NaCl.

After removal of the insoluble debris by centrifugation, the protein is precipitated by the addition of 3 volumes of saturated aqueous ammonium sulfate. The enzyme is pelleted, resuspended in RT buffer (50 mM Tris pH 7.5, 1 mM EDTA, 5 mM DTT, 0.1% NP-40, 0.1M NaCl, and 50% glycerol), and stored at −70° C. for further use.

b) Composition of 2× concentrated stock reaction mixture

| Stock Reagent | 2X Mix Concentration |
|---|---|
| 1M Tris pH 7.4 | 100 mM |
| 1M Dithiothreitol | 40 mM |
| 1M NaCl | 120 mM |
| 1% Nonidet P-40 | 0.1% |
| 1M MgCl | 4 mM |
| [poly r(C)/oligo d(G)](5:1) | 2 μg/mL |
| $^3$H-dGTP (81 μM) | 0.6 μM |

Assay Procedure:

The 2× concentrated stock reaction mixture is aliquoted and stored at −20° C. The mixture is stable and thawed for use in each assay. This enzyme assay has been adapted to a 96 well microtiter plate system, and has been previously described (6). Tris buffer (50 mM, pH 7.4), vehicle (solvent diluted to match the compound dilution), or compounds in vehicle are dispensed into 96-well microtiter plates (10 μL/well; 3 wells/compound). The HIV-1 RT enzyme is thawed, diluted in 50 mM Tris pH 7.4 so that fifteen μL of diluted enzyme contain 0.001 Unit (one unit is that amount of enzyme to transform 1 micromole of substrate per minute at 25° C.), and fifteen μL are dispensed per well. Twenty μL of 0.12–0.5M EDTA are added to the first three wells of the microtiter plate. EDTA chelates the Mg$^{++}$ present and prevents reverse transcription. This group serves as background polymerization which is subtracted from all other groups. Twenty-five μl of the 2× reaction mixture are added to all wells and the assay is allowed to incubate at room temperature for 60 minutes. The assay is terminated by precipitating the DNA in each well with 50μL of 10% trichloracetic acid (TCA) (10% w/v) in sodium pyrophosphate (1% w/v). The microtiter plate is incubated for 15 minutes at 4° C. and the precipitate is fixed onto #30 glass fiber paper (Schleicher & Schuell) using a Skatron semi-automatic harvester. The filters are then washed with additional TCA (5%) containing sodium pyrophosphate (1%), rinsed with aqueous ethanol (70%), dried, and transferred to scintillation vials (6). Each vial receives 2 mL of scintillation cocktail and is counted in a Beckman beta counter.

The calculation for percent inhibition is as follows:

$$\% \text{ inhibition} = \frac{CPM \text{ Mean Test Value} - CPM \text{ Mean Control Value} \times 100}{CPM \text{ Mean Control Value}}$$

References:
1. Benn, S., et al., *Science* 230:949, 1985
2. Farmerie, W. G. et. al., *Science* 236:305, 1987
3. Yanisch-Perron, C., Viera, J., and Messing, J., *Gene* 33:103, 1985
4. International Biotechnologies, Inc., New Haven, Conn. 06535
5. Maniatis, T, Fritsch, E. F., and J. Sambrook, eds. *Molecular Cloning: A Laboratory Manual*, Cold Spring Harbor Laboratory, 1982
6. Spira, T., et. al. *J. Clinical Microbiology*, 25:97, 1987.

TABLE I

| Ex. No. Example | RT (WT) Assay % inh. (1 μM) | RT (Y181C) Assay % inh. (1 μM) |
|---|---|---|
| 1. | 96 | 90 |
| 2. | 97 | 91 |
| 3. | 92 | 68 |
| 4. | 94 | 52 |
| 5. | 89 | 36 |
| 6. | 91 | 58 |
| 7. | 83 | 46 |
| 8. | 72 | 32 |
| 9. | 91 | 70 |
| 10. | 72 | 12 |
| 11. | 84 | 25 |
| 12. | 96 | 89 |

EXAMPLES

The following examples further illustrate the present invention, and will enable others skilled in the art to understand it more completely. It should be understood, however, that the invention is not limited to the particular examples given below.

Example 1

8-Ethyl-thienyl[3',4':6,5]dipyrido[2,3-b:3',2'-f]azepine

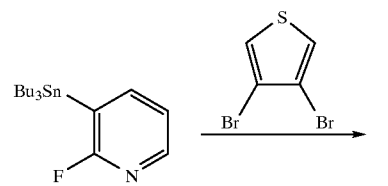

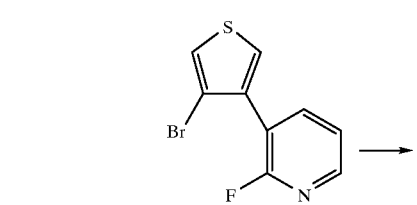

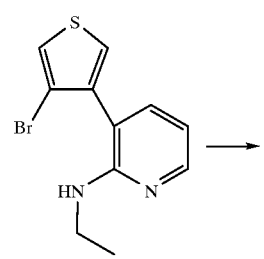

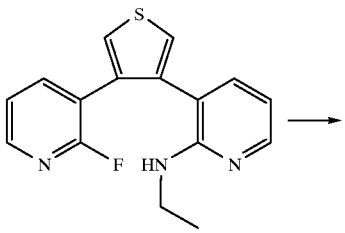

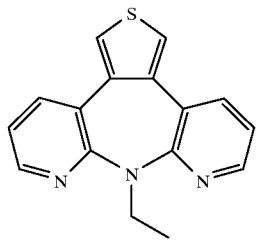

(a) 2-Fluoro-3-tributylstannylpyridine.

To a mixture of lithium diisopropylamide (1.5M in cyclohexane, 43 mL) and tetrahydrofuran (60 mL) cooled to −70° C. was added 2-fluoropyridine (6.0 mL) at such a rate that the temperature remained below −70° C. After 1.5 hours, tributyltin chloride (15 mL) was added, and the mixture was allowed to warm to room temperature. The mixture was diluted with hexane, washed with water, dried, filtered, and evaporated. Chromatography of the residue over silica gel (cyclohexane/ethyl acetate 98/2) gave 2-fluoro-3-tributylstannylpyridine (17 g).

(b) 3-Bromo-4-(2-fluoropyridin-3-yl)thiophene.

A mixture of 2-fluoro-3-tributylstannylpyridine (1.9 g), 3,4-dibromothiophene (1.5 g) and Pd(Ph₃P)₂Cl₂ (0.175 g) in N-methylpyrrolidinone (7.5 mL), in a sealed tube, was heated at 100° C. for 16 hours. The mixture was cooled and stirred with aqueous potassium fluoride for 6 hours. The mixture was diluted with ethyl acetate, washed with water, dried filtered and evaporated. The residue was fractionated by chromatography to give 3-bromo-4-(2-fluoropyridin-3-yl)thiophene (0.35 g), mp 48–50° C.

(c) 3-Bromo-4-(2-ethylaminopyridin-3-yl)thiophene.

A solution of 3-bromo-4-(2-fluoropyridin-3-yl)thiophene (0.344 g) and ethylamine (0.2 g) in dioxane (1 mL), in a sealed tube, was heated at 100° C. for four days. The mixture was cooled, diluted with ethyl acetate, washed with water, dried, filtered, and evaporated. The residue was fractionated by chromatography to give 3-bromo-4-(2-ethylaminopyridin-3-yl)thiophene (0.316 g) as an oil.

(d) 3-(2-Fluoropyridin-3-yl)-4-(2-ethylaminopyridin-3-yl)thiophene.

A mixture of 3-bromo-4-(2-ethylaminopyridin-3-yl) thiophene (0.31 g), 2-fluoro-3-tributylstannylpyridine (0.507 g) and Pd(Ph₃P)₂Cl₂ (0.035 g) in N-methylpyrrolidinone (3 mL), in a sealed tube, was heated at 100° C. for 17 hours. The mixture was cooled and tetrabutylammonium fluoride (1M in tetrahydrofuran, 1 mL) was added. After one day, the mixture was diluted with ethyl acetate, washed with water, dried, filtered, and evaporated. The residue was fractionated by chromatography to give 3-(2-fluoropyridin-3-yl)-4-(2-ethylaminopyridin-3-yl)thiophene (0.077 g) mp 127–129° C.

(e) 8-Ethyl-thienyl[3',4':6,5]dipyrido[2,3-b:3',2'-f]azepine.

To a solution of 3-(2-fluoropyridin-3-yl)-4-(2-ethylaminopyridin-3-yl)thiophene (0.021 g) in tetrahydrofuran (1.5 mL was added potassium bistrimethylsilylamide (0.5M in toluene) until no yellow color appeared on addition of further reagent. The mixture was stirred for 5 minutes, ethanol was added, the mixture was diluted with ethyl acetate, washed with water, dried, filtered and evaporated. The residue was fractionated by chromatography to give 8-ethyl-thienyl[3',4':6,5]dipyrido[2,3-b:3',2'-f]azepine mp 140–142° C.

Example 2

6-Chloro-8-ethyl-thienyl[3',4':6,5]dipyrido[2,3-b:3',2'-f]azepine

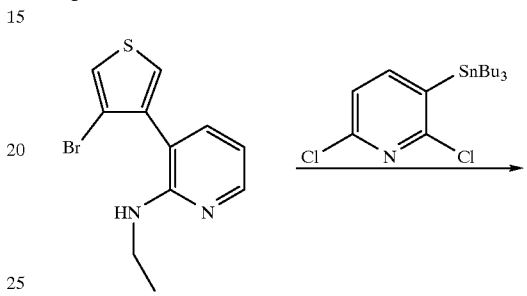

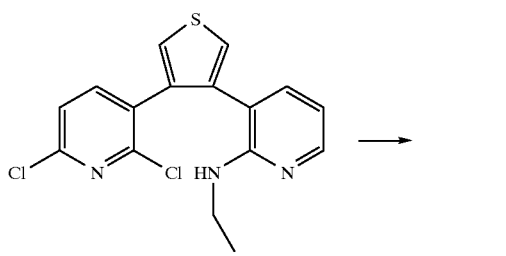

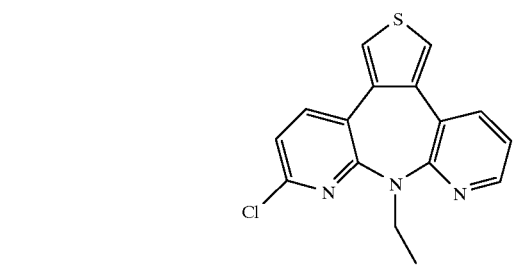

(a) 2, 6-dichloro-3-tributylstannylpyridine.

To a mixture of lithium diisopropylamide (1.5M in cyclohexane, 9.0 mL), and tetrahydrofuran (20 mL) cooled to −70° C. was added 2,6 dichloropyridine (2.0 g, 13.5 mmol) in tetrahydrofuran (25 mL), keeping the temperature below −60° C. The mixture was stirred for 30 minutes, tributyltin chloride (3.7 mL, 13.5 mmol) was added dropwise, and the mixture was allowed to warm to room temperature. Ethyl acetate was added, and the mixture was washed with water, dried, filtered, and evaporated. Chromatography of the residue over silical gel (eluent, 3% ethyl acetate/hexane) gave 2, 6-dichloro-3-tributylstannylpyridine 2, 6-dichloro-3-tributylstannylpyridine (4.0 g).

(b) 6-Chloro-8-ethyl-thienyl[3',4':6,5]dipyrido[2,3-b:3', 2'-f]azepine.

A mixture of 3-bromo-4-(2-ethylaminopyridin-3-yl) thiophene [synthesis described above] (0.757 g), 2, 6-dichloro-3-tributylstannylpyridine (1.331 g), triphenylarsine (0.261 g), and trisdibenzylideneacetone dipalladium (0.092 g) in N-methylpyrrolidinone (3 mL) was heated at 100° C. for 48 hours. Tetrabutylammonium fluoride (1M in tetrahydrofuran, 3 mL) was added . After 2 hours, the mixture was diluted with ethyl acetate, washed with water, dried, filtered and evaporated. The residue was fractionated by chromatography to give 3-(2,6-dichloropyridin-3-yl)-4-(2-ethylaminopyridin-3-yl)thiophene (0.059 g) which was used directly in the next step. To a solution of 3-(2,6-dichloropyridin-3-yl)-4-( 2-ethylaminopyridin-3-yl) thiophene (0.059 g) in tetrahydrofuran (2 mL) was added sodium hexamethyldisilazide (1 molar in tetrahydrofuran, 1 mL). After 20 minutes, the reaction was quenched with methanol, diluted with ethyl acetate, washed with water, dried, filtered and evaporated. The residue was fractionated by chromatography to give 6-chloro-8-ethyl-thienyl[3',4':6,5]dipyrido[2,3-b:3',2'-f]azepine (0.024 g) mp 139–141° C.

Example 3

6-(Pyrazol-4-yl)-8-ethyl-thienyl[3',4':6,5]dipyrido[2,3-b:3',2'-f]azepine

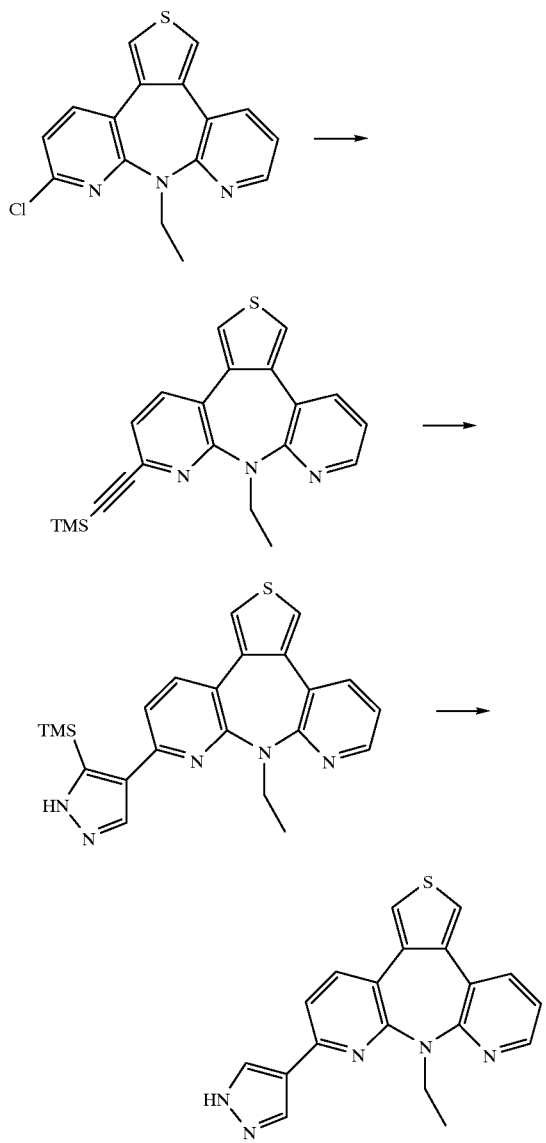

A mixture of 6-chloro-8-ethyl-thienyl[3',4':6,5]dipyrido[2,3-b:3',2'-f]azepine (0.02 g), triethylamine (0.3 g), trimethylsilylacetylene (0.158 g), copper(1) iodide (0.0021 g), and Pd(Ph₃P)₂Cl₂ (0.0046 g) was heated in a sealed tube at 85° C. for 24 hours. The mixture was diluted with hexane/ethyl acetate, washed with water, dried filtered and evaporated. The residue was fractionated by chromatography to give 6-(trimethylsilylethynyl)-8-ethyl-thienyl[3',4':6,5]dipyrido[2,3-b:3',2'-f]azepine which was used directly in the next reacaction. The 6-(trimethylsilylethynyl)-8-ethyl-thienyl[3',4':6,5]dipyrido[2,3-b:3',2'-f]azepine was dissolved in ethereal diazomethane (2M, 0.5 mL). The mixture was stirred for 28 hours, evaporated to dryness, taken up in tetrahydrofuran, and tetrabutylammonium fluoride (1M in tetrahydrofuran, 0.5 mL) was added. After 5 minutes, the mixture was diluted with ethyl acetate, washed with water, dried, filtered and evaporated. The residue was fractionated by chromatography to give 6-(pyrazol-4-yl)-8-ethyl-thienyl [3',4':6,5]dipyrido[2,3-b:3', 2'-f]azepine (0.011 g). mp 250–252° C.

Example 4: 8-Ethyl-1-methyl-thienyl[3',4':6,5]dipyrido[2,3-b:3',2'-f]azepine and Example 5: 8-ethyl-1,3-dimethyl-thienyl[3',4':6,5]dipyrido[2,3-b:3',2'-f]azepine

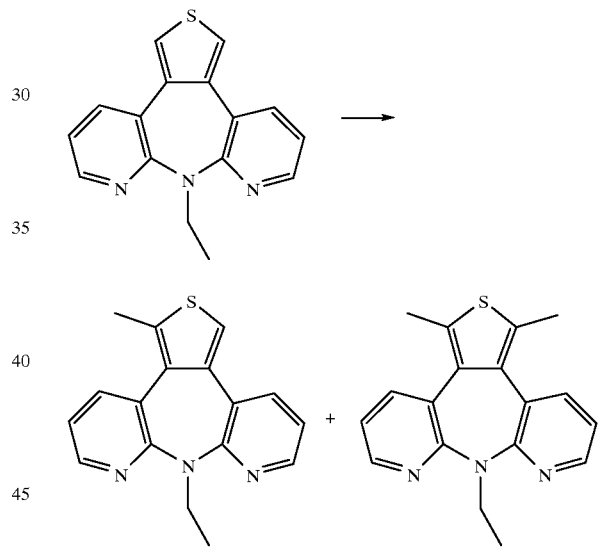

To a solution of 8-ethyl-thienyl[3',4':6,5]dipyrido[2,3-b:3',2'-f]azepine (0.025 g) in tetrahydrofuran (2 mL) cooled to −78° C. was added lithium diisopropylamide (1.5M in cyclohexane, 0.1 mL). After 10 minutes, iodomethane (2 drops) was added, and the mixture was allowed to warm to room temperature. The mixture was diluted with ethyl acetate, washed with water, dried, filtered and evaporated. The residue was dissolved in tetrahydrofuran (2 mL) cooled to −78° C., and lithium diisopropylamide (1.5M in cyclohexane, 0.1 mL) was added. After 10 minutes, iodomethane (0.05 mL) was added, and the mixture was allowed to warm to room temperature. The mixture was diluted with ethyl acetate, washed with water, dried, filtered and evaporated. The residue was fractionated by HPLC to give 8-ethyl-1-methyl-thienyl[3',4':6,5]dipyrido[2,3-b:3',2'-f]azepine (0.010 g) mp 106–108° C. and 8-ethyl-1,3-dimethyl-thienyl[3',4':6,5]dipyrido[2,3-b:3',2'-f]azepine (0.003 g) mp 176–178° C.

Example 6

8-Ethyl-thienyl[2',3':6,5]dipyrido[2,3-b:3',2'-f]azepine

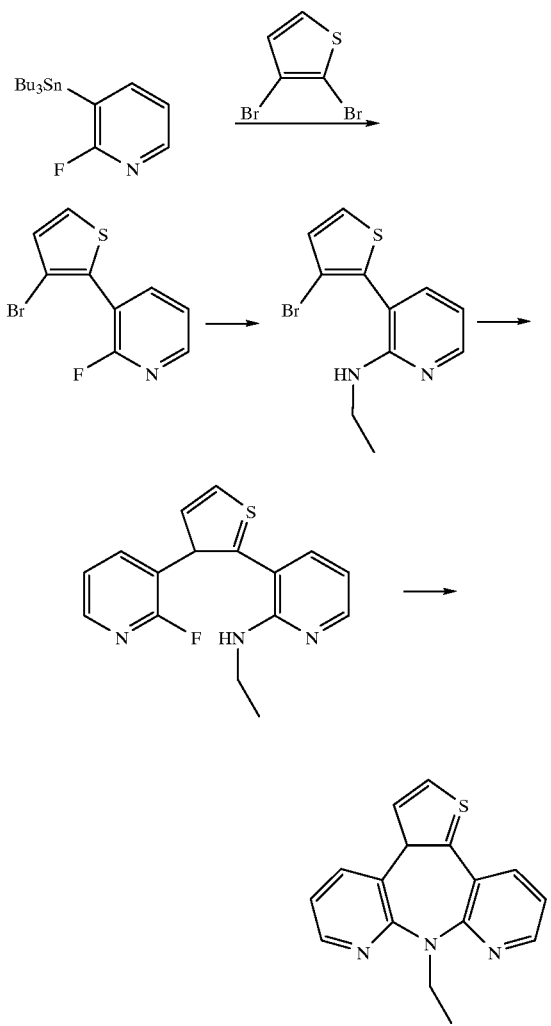

(a) 3-Bromo-2-(2-fluoropyridin-3-yl)thiophene.

A mixture of 2,3-dibromothiophene (2.86 g), 2-fluoro-3-tributylstannylpyridine (3.93 g), Pd(Ph$_3$P)$_2$Cl$_2$ (0.153 g) in N-methylpyrrolidinone (25 mL) was heated at 75° C. under argon for 3.5 hours. Tetrabutylammonium fluoride (1M in tetrahydrofuran, 10 mL) was added and the mixture was stirred for 3 hours. The mixture was diluted with ethyl acetate, washed with water, dried, filtered and evaporated. Chromatography of the residue over silica gel gave 3-bromo-2-(2-fluoropyridin-3-yl)thiophene (1.07 g) as an oil.

(b) 3-Bromo-2-(2-ethylaminopyridin-3-yl)thiophene.

A mixture of 3-bromo-2-(2-fluoropyridin-3-yl)thiophene (0.47 g) and ethylamine (0.4 g) in dioxane (2 mL) in a sealed tube was heated at 100° C. for 2 days. The mixture was diluted with ethyl acetate, washed with water, dried, filtered and evaporated to give 3-bromo-2-(2-ethylaminopyridin-3-yl)thiophene (0.45 g).

(c) 3-(2-fluoropyridin-3-yl)-2-(2-ethylaminopyridin-3-yl)thiophene.

A mixture of 3-bromo-2-(2-ethylaminopyridin-3-yl)thiophene (0.085 g), 2-fluoro-3-tributylstannylpyridine (0.26 g) and Pd(Ph$_3$P)$_2$Cl$_2$ (0.014 g) in N-methylpyrrolidinone (2 mL) was heated at 75° C. under argon for 1 day. The mixture was diluted with ethyl acetate, washed, dried, filtered and evaporated. The residue was chromatographed to give 3-(2-fluoropyridin-3-yl)-2-(2-ethylaminopyridin-3-yl)thiophene (0.028 g). mp 86–89° C.

(d) 8-Ethyl-thienyl[2',3':6,5]dipyrido[2,3-b:3',2'-f] azepine.

To a solution of 3-(2-fluoropyridin-3-yl)-2-(2-ethylaminopyridin-3-yl)thiophene (0.028 g) in tetrahydrofuran (1.5 mL) was added KHMDS (0.5M in toluene, 0.5 mL). The mixture was quenched with methanol and evaporated to dryness. The residue was fractionated by preparative layer chromatography to give 8-ethyl-thienyl[2',3':6,5]dipyrido[2,3-b:3',2'-f]azepine (0.006 g) mp 158–160° C.

Example 7

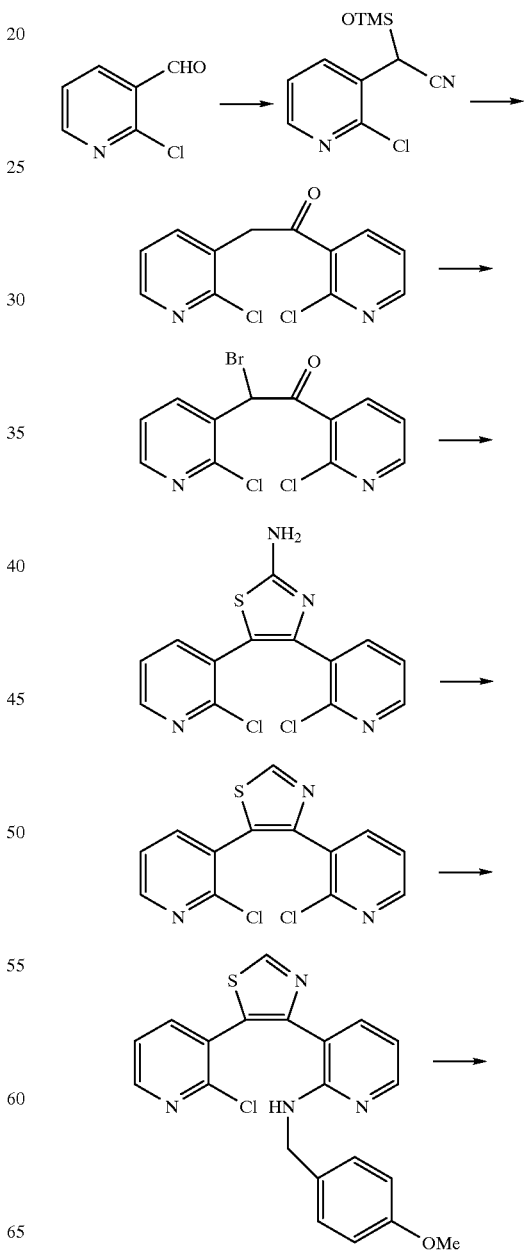

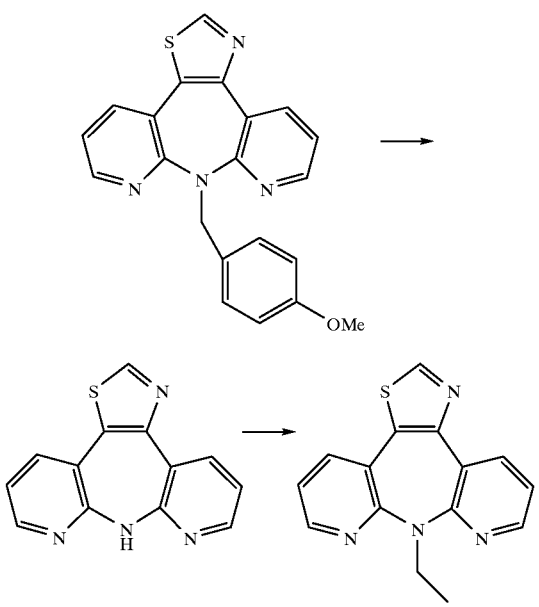

8-Ethyl-thiazolo[4',5':6,5]dipyrido[2,3-b:3',2'-f]azepine (a) 2-chloro-3-[(2-chloropyridin-3-yl)acetyl]pyridine.

A mixture of 2-chloropyridone-3-carboxaldehyde (0.132 mol) and trimethylsilyl cyanide (13.1 g) was stirred at 50–60° C. for 4 hours in the presence of zinc iodide (10 mg), and then overnight at room temperature. The mixture was diluted with tetrahydrofuran (70 mL), and added slowly to a solution of lithium diisopropylamide (1.5M in cyclohexane, 130 mL) in tetrahydrofuran (130 mL) keeping the temperature below −65° C. After 30 minutes 2-chloro-3-chloromethylpyridine (21.4 g) in tetrahydrofuran (20 mL)was added slowly. After stirring at −70° C. for 30 minutes the mixture was allowed to warm to room temperature. Water was added, and the mixture was extracted with methylene chloride. The organic phase was dried, filtered, and evaporated. Chromatography of the residue over silica gel (ethyl acetate/hexane 1/1) gave 2-chloro-3-[(2-chloropyridin-3-yl)acetyl]pyridine (27.7 g) as an oil. 2-chloro-3-[2-bromo-2-(2-chloropyridin-3-yl)acetyl]pyridine. To a solution of bromine (0.125 g) in acetic acid (1 mL) was added slowly a solution of 2-chloro-3-[(2-chloropyridin-3-yl)acetyl]pyridine (0.21 g) in acetic acid (5 mL). The mixture was stirred overnight at room temperature. The mixture was diluted with water, and extracted with methylene chloride. The organic phase was dried ($Na_2SO_4$) filtered and evaporated. The residue was purified by chromatography over silica gel (ethyl acetate/hexane ) to give chloro-3-[2-bromo-2-(2-chloropyridin-3-yl)acetyl]pyridine (0.224 g).

(b) 4, 5-di-(2-chloropyridin-3-yl)-2-aminothiazole.

A solution of 2-chloro-2-[2-bromo-2-(2-chloropyridin-3-yl)acetyl]pyridine (0.170 g), and thiourea (0.040 g) in ethanol (5 mL) was heated at 70–75° C. for 2 hours. The solvent was evaporated, and the residue was recrystallized from ethanol to give 4, 5-di-(2-chloropyridin-3-yl)-2-aminothiazole (0.030 g). mp 273–274° C.

(c) 4, 5-di-(2-chloropyridin-3-yl)thiazole.

To a solution of 4, 5-di-(2-chloropyridin-3-yl)-2-aminothiazole (0.060 g) in tetrahydrofuran (5 mL) was added butylnitrite (0.060 g). The mixture was heated under reflux for 3 hours. Further butylnitrite was added, and heating was continued for 2 hours. The solvent was evaporated, and the residue was fractionated by chromatography over silica gel to give 4, 5-di-(2-chloropyridin-3-yl) thiazole (0.035 g) as a solid.

(d) 4-[2-(4-methoxybenzylamino)pyridin-3-yl]- 5-(2-chloropyridin-3-yl)thiazole.

A mixture of 4,5-di-(2-chloropyridin-3-yl)thiazole (0.047 g), 4-methoxybenzylamine (0.021 g), and diisopropylethylaamine (0.025 g) in xylene was heated in a sealed tube at 130° C. for 4 days. The solvent was evaporated, and the residue was fractionated by chromatography to give 4-[2-(4-methoxybenzylamino)pyridin-3-yl]-5-(2-chloropyridin-3-yl)thiazole (0.015 g).

(e) 8-(4-methoxybenzyl)-thiazolo[4',5':6,5]dipyrido[2,3-b:3',2'-f]azepine.

To a solution of 4-[2-(4-methoxybenzylamino)pyridin-3-yl]-5-(2-chloropyridin-3-yl)thiazole (0.045 g) in tetrahydrofuran (10 mL) was added sodium bistrimethylsilylamide (1M in tetrahydrofuran, 1.1 mL). The reaction mixture was stirred for 0.5 hours. The solvent was evaporated, the residue was taken up in methylene chloride, washed with water, dried ($Na_2SO_4$), filtered and evaporated. The residue was fractionated by chromatography over silica gel to give 8-(4-methoxybenzyl)-thiazolo[4',5':6,5]dipyrido[2,3-b:3',2'-f]azepine as an oil (0.320 g).

(f) Thiazolo[4',5':6,5]dipyrido[2,3-b:3',2'-f]azepine.

A solution of 8-(4-methoxybenzyl)-thiazolo[4',5':6,5] dipyrido[2,3-b:3',2'-f]azepine (0.32 g) in trifluoroacetic acid was left at room temperature for 3 hours. The mixture was diluted with water, and extracted with methylene chloride. The organic phase was dried, filtered and evaporated to give crystalline thiazolo[4',5':6,5]dipyrido[2,3-b:3',2'-f]azepine (0.21 g). mp 212–213° C.

(g) 8-Ethyl-thiazolo[4',5':6,5]dipyrido[2,3-b:3',2'-f] azepine.

To a solution of thiazolo[4',5':6,5]dipyrido[2,3-b:3',2'-f] azepine (0.09 g) in dimethylformamide (6 mL) was added sodium hydride (0.033 g). Ethyl iodide (0.15 g) was added, and the mixture was stirred for 2 hours. The solvent was evaporated, and the residue was fractionated by chromatography to give 8-ethyl-thiazolo[4',5':6,5]dipyrido[2,3-b:3',2'-f]azepine (0.085 g). mp 167–168° C.

Example 8

8-Ethyl-oxazolo[4',5':6,5]dipyrido[2,3-b:3',2'-f]azepine

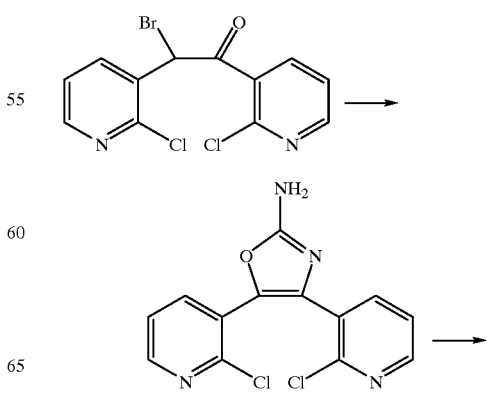

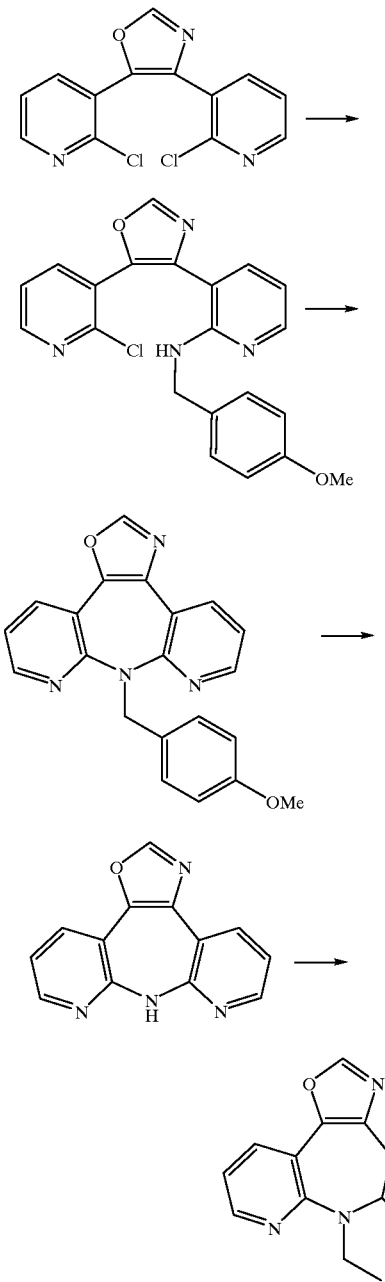

a) 4, 5-di-(2-chloropyridin-3-yl)-2-aminooxaazole.

A solution of 2-chloro-2-[2-bromo-2-(2-chloropyridin-3-yl)acetyl]pyridine (0.062 g), and urea (0.054 g) in dimethylformamide (4 mL) was heated at 105° C. for 4 hours. The solvent was evaporated, and the residue was diluted with methylene chloride, washed with water, dried, filtered and evaporated. The residue was fractionated by chromatography over silica gel to give 4, 5-di-(2-chloropyridin-3-yl)-2-aminooxazole (0.030 g). mp 243–244° C.

(b) 4, 5-di-(2-chloropyridin-3-yl)oxazole.

To a solution of 4, 5-di-(2-chloropyridin-3-yl)-2-aminooxazole (0.030 g) in tetrahydrofuran (3 mL) was added butylnitrite (0.033 g). The mixture was heated under reflux for 3 hours. The solvent was evaporated, and the residue was fractionated by chromatography to give 4, 5-di-(2-chloropyridin-3-yl)oxazole (0.010 g) as a solid. mp 157–158° C.

(c) 8-(4-methoxybenzyl)-oxazolo[4',5':6,5]dipyrido[2,3-b:3',2'-f]azepine.

A mixture of 4, 5-di-(2-chloropyridin-3-yl)oxazole (0.120 g), and 4-methoxybenzylamine (0.270 g), and diisopropyl-ethylamine (0.100 g) in xylene (10 mL) was heated in a sealed tube at 130° C. for 4 days. The solvent was evaporated, and the residue was fractionated by chromatography to give 8-(4-methoxybenzyl)-oxazolo[4',5':6,5] dipyrido[2,3-b:3',2'-f]azepine (0.062 g).

(d) Oxazolo[4',5':6,5]dipyrido[2,3-b:3',2'-f]azepine.

A solution of 8-(4-methoxybenzyl)-oxazolo[4',5':6,5] dipyrido[2,3-b:3',2'-f]azepin (0.030 g) in trifluoroacetic acid (3 mL) was left at room temperature for 1 hour. The solvent was evaporated to give oxazolo[4',5':6,5]dipyrido[2,3-b:3',2'-f]azepine (0.030 g).

(e) 8-Ethyl-oxazolo[4',5':6,5]dipyrido[2,3-b:3',2'-f] azepine.

To a solution of oxazolo[4',5':6,5]dipyrido[2,3-b:3',2'-f] azepine (0.030 g) in dimethylformamide (3 mL) was added sodium hydride (0.030 g). Ethyl iodide (0.100 g) was added, and the mixture was stirred for 2 hours. The solvent was evaporated, and the residue was fractionated by chromatography over silica gel to give 8-ethyl-oxazolo[4',5':6,5] dipyrido[2,3-b:3',2'-f]azepine (0.031 g). mp 167–168° C.

Example 9

8-Ethyl-(1, 2, 3)thiadiazolo[4',5':6,5]dipyrido[2,3-b:3',2'-f]azepine

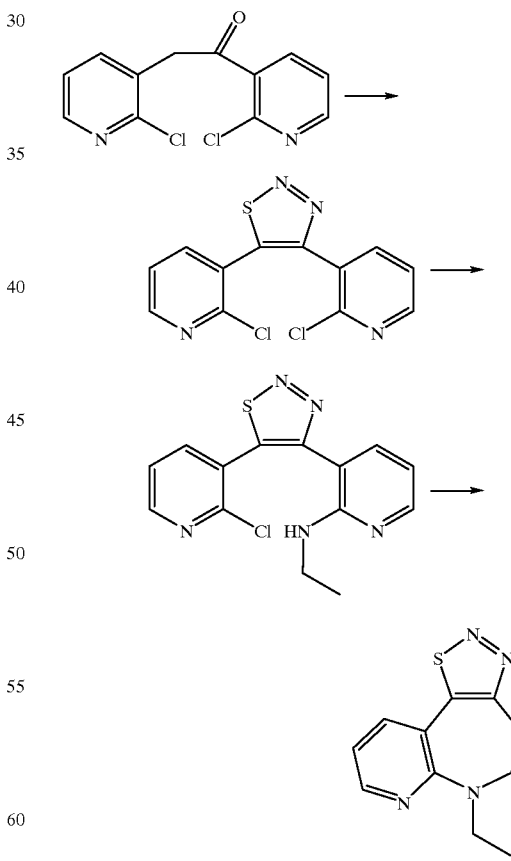

(a) 4, 5-di-(2-chloropyridin-3-yl)-1, 2, 3-thiadiazole.

A mixture of (2-chloropyridin-3-yl)methyl-(2-chloropyridin-3-yl)ketone (0.273 g), ethyl carbazate (0.103 g), and p-toluenesulfonic acid monohydrate (0.010 g) in toluene (2 mL) was heated at 110° C. for 3 hours. The mixture was evaporated to dryness, and the residue was taken up in thionyl chloride 3 mL and heated at 70° C. for 1 hour. The mixture was added cautiously to aqueous potassium carbonate, and extracted with ethyl acetate. The organic phase was dried, filtered and evaporated. Chromatography of the residue over silica gel gave 4, 5-di-(2-chloropyridin-3-yl)-1, 2, 3-thiadiazole (0.269 g). mp 146–148° C.

(b) 4-(2-chloropyridin-3-yl)-5-(2-ethylaminopyridin-3-yl)- 1, 2, 3-thiadiazole.

A mixture of 4, 5-di-(2-chloropyridin-3-yl)-1, 2, 3-thiadiazole (1.823 g), and ethylamine (0.61 g) in dioxane (9 mL) was heated at 105° C. in a sealed tube 3 days. The mixture was diluted with ethyl acetate, washed with water, dried, filtered and evaporated. Chromatography of the residue over silica gel gave 4-(2-chloropyridin-3-yl)-5-(2-ethylaminopyridin-3-yl)-1, 2, 3-thiadiazole (1.243 g) as an oil.

(c) 8-Ethyl-(1, 2, 3)thiadiazolo[4',5':6,5]dipyrido[2,3-b:3', 2'-f]azepine.

To a solution of 4-(2-chloropyridin-3-yl)-5-(2-ethylaminopyridin-3-yl)-1, 2, 3-thiadiazole (0.700 g) in tetrahydrofuran (5 mL) was added potassium bistrimethylsilylamide (0.5M in toluene, 3.5 mL). After 10 minutes the mixture was diluted with ethyl acetate, washed with water, dried, filtered and evaporated. Chromatography of the residue over silica gel gave 8-ethyl-(1, 2, 3)thiadiazolo[4',5':6,5]dipyrido[2,3-b:3',2'-f]azepine (0.453 g). mp 194–196° C.

Example 10

6-Bromo-8-Ethyl-(1, 2, 3)thiadiazolo[4',5':6,5]dipyrido[2,3-b:3',2'-f]azepine

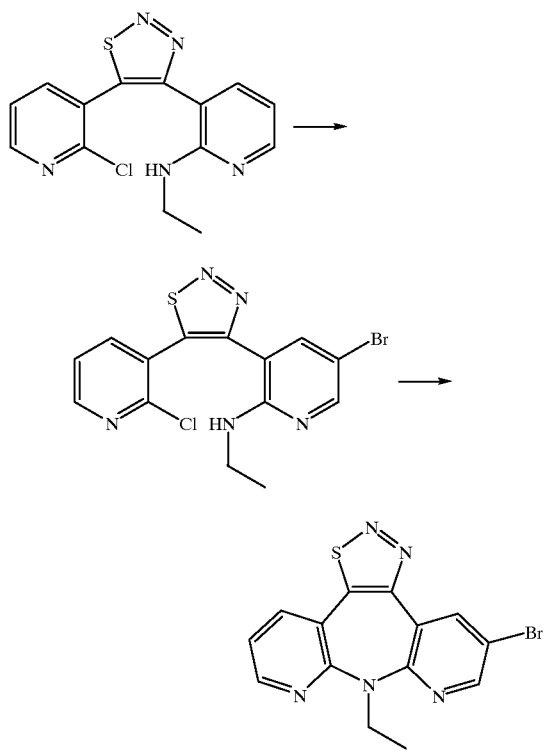

(a) 4-(2-chloropyridin-3-yl)-5-(2-ethylamino-5-bromo-pyridin-3-yl)-1, 2, 3-thiadiazole.

To a solution of 4-(2-chloropyridin-3-yl)-5-(2-ethylaminopyridin-3-yl)-1, 2, 3-thiadiazole (0.324 g) in acetic acid (4 mL) containing sodium acetate (0.098 g) was added dropwise a solution of bromine (0.185 g) in acetic acid (1 mL). After 5 minutes, the mixture was diluted with ethyl acetate, washed with aqueous potassium carbonate, dried, filtered and evaporated. Chromatography of the residue over silica gel (ethyl acetate/hexane/chloroform 1/3/0.5) gave 4-(2-chloropyridin-3-yl)-5-(2-ethylamino-5-bromo-pyridin-3-yl)-1, 2, 3-thiadiazole (0.329 g).

(b) 5-Bromo-8-ethyl-(1, 2, 3)thiadiazolo[4',5':6,5]dipyrido[2,3-b:3',2'-f]azepine.

To a solution of 4-(2-chloropyridin-3-yl)-5-(2-ethylamino-5-bromo-pyridin-3-yl)-1, 2, 3-thiadiazole (0.292 g) in tetrahydrofuran (3 mL) was added potassium bistrimethylsilylamide (0.5M in toluene, 2.0 mL). After 10 minutes, the mixture was diluted with ethyl acetate, washed with water, dried, filtered and evaporated. The residue was crystallized from hexane/chloroform to give 5-bromo-8-ethyl-(1, 2, 3)thiadiazolo[4',5':6,5]dipyrido[2,3-b:3',2'-f]azepine (0.215 g).

Example 11

6-Ethynyl-8-ethyl-(1, 2, 3)thiadiazolo[4',5':6,5]dipyrido[2,3-b:3',2'-f]azepine

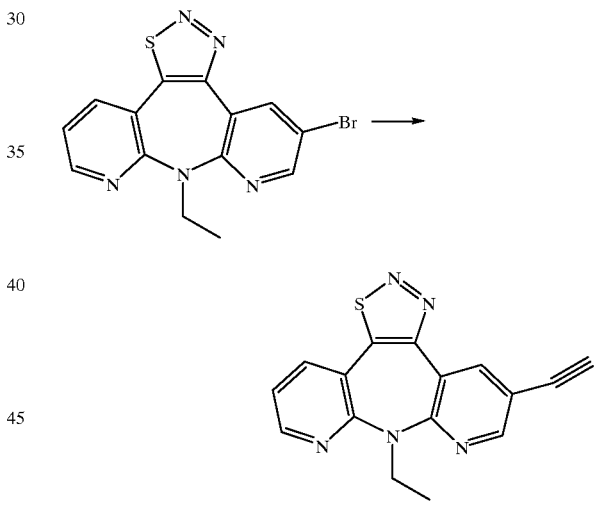

A mixture of 5-bromo-8-ethyl-(1, 2, 3)thiadiazolo[4',5':6, 5]dipyrido[2,3-b:3',2'-f]azepine (0.198 g), Pd(Ph$_3$P)$_2$Cl$_2$ (0.015 g), CuI (0.005 g) trimethylsilylacetylene (0.12 g), and triethylamine (2 mL) in dimethylformamide (1 mL) was heated at 100° C. in a sealed tube for 1 hour. The mixture was diluted with ethyl acetate, washed with water, dried, filtered and evaporated. Chromatography of the residue over silica gel (ethyl acetate/hexane/methylene chloride 1/0.2/ 0.2) gave 6-trimethylsilylethynyl-8-ethyl-(1, 2, 3)thiadiazolo[4',5':6,5]dipyrido[2,3-b:3',2'-f]azepine (0.202 g). This product was taken up in tetrabutylammonium fluoride (1M in tetrahydrofuran, 2 mL), and left at room temperature for 1.5 hours. The mixture was diluted with ethyl acetate, washed with water, dried, filtered and evaporated. Chromatography of the residue over silica gel (methylene chloride) gave 6-ethynyl-8-ethyl-(1, 2, 3)thiadiazolo[4',5':6, 5]dipyrido[2,3-b:3',2'-f]azepine (0.124 g), mp 200–202° C.

Example 12

6-Phenylethyl-8-ethyl-(1, 2, 3)thiadiazolo[4',5':6,5]dipyrido[2,3-b:3',2'-f]azepine

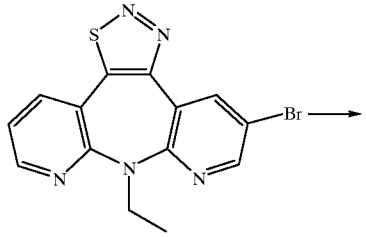

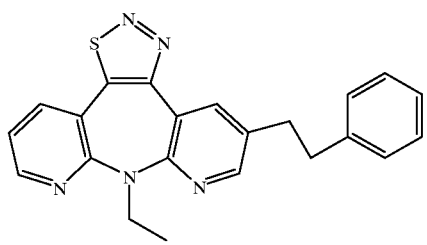

A mixture of 6-ethynyl-8-ethyl-(1, 2, 3)thiadiazolo[4', 5':6,5]dipyrido[2,3-b:3', 2'-f]azepine (0.103 g), iodobenzene (0.440 g), Pd(Ph$_3$P)$_2$Cl$_2$ (0.016 g), CuI (0.017 g), and triethylamine (1 mL) in dimethylformamide (1 mL) was heated at 100° C. in a sealed tube for 2 hours. The mixture was diluted with ethyl acetate, washed with water, dried, filtered and evaporated. Chromatography of the residue over silica gel (methylene chloride) gave 6-phenylethynyl-8-ethyl-(1, 2, 3)thiadiazolo[4',5':6,5]dipyrido[2,3-b:3',2'-f]azepine (0.061 g). A mixture of this product, and 10% Pd/C (0.066 g) in ethanol (15 mL) was hydrogenated in a Parr apparatus for 22 hours. The catalyst was removed by filtration and the solvent evaporated. Fractionation of the residue by preparative layer chromatography (developer, methylene chloride) gave 6-phenylethyl-8-ethyl-(1, 2, 3)thiadiazolo[4', 5':6,5]dipyrido[2,3-b:3',2'-f]azepine (0.01 g).

EXAMPLE A

Capsules or Tablets

| A-1 | | A-2 | |
|---|---|---|---|
| Ingredients | Quantity | Ingredients | Quantity |
| Compound of Ex. 1 | 250 mg | Compound of Ex. 1 | 50 mg |
| Starch | 160 mg | Dicalcium Phosphate | 160 mg |
| Microcrys. Cellulose | 90 mg | Microcrys. Cellulose | 90 mg |
| Na Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of Example 1 is blended into a powder mixture with the premixed excipient materials as identified above with the exception of the lubricant. The lubricant is then blended in and the resulting blend compressed into tablets or filled into hard gelatin capsules.

EXAMPLE B

Parenteral Solutions

| Ingredients | Quantity |
|---|---|
| Compound of Example 1 | 500 mg |
| Tartaric acid | 1.5 g |
| Benzyl Alcohol | 0.1% by weight |
| Water for injection | q.s. to 100 mL |

The excipient materials are mixed with the water, and thereafter the compound of Example 1 is added. Mixing is continued until the solution is clear. The pH of this solution is adjusted to 3.0, and is then filtered into the appropriate vials or ampoules and sterilized by autoclaving.

EXAMPLE C

Nasal Solutions

| Ingredients | Quantity |
|---|---|
| Compound of Example 1 | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 mL |

The excipient materials are mixed with the water, and thereafter the compound of Example 1 is added and mixing is continued until the solution is clear. The pH of this solution is adjusted to 4.0, and is then filtered into the appropriate vials or ampoules.

What is claimed is:

1. A compound of formula I, formula II or formula III

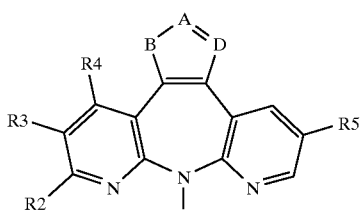

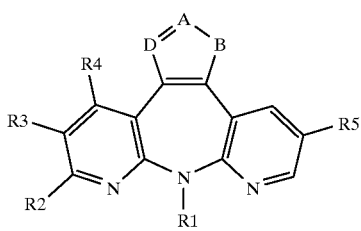

-continued

[structure with R4, R3, R2, N-R1, N, R5, A, B, D]

wherein:
in formula I, formula II and in formula III, A and D are carbon (unsubstituted or optionally substituted with methyl, ethyl, isopropyl, vinyl, isopropenyl, ethynyl, halogen, nitro, cyano, amino, methylamino, dimethylamino, hydroxy, methoxy, mercapto or methylthio) or nitrogen, and B is oxygen, sulfur or nitrogen (unsubstituted or optionally substituted with methyl, ethyl, isopropyl, hydroxy or methoxy);
and,
$R_1$ is a hydrogen atom, alkyl of 1 to 4 carbon atoms, fluoroalkyl of 1 to 4 carbon atoms and 1 to 3 fluorine atoms, cycloalkyl of 3 to 6 carbon atoms, oxetanyl, thietanyl, tetrahydrofuranyl, tetrahydrothienyl, tetrahydropyranyl, tetrahydrothiopyranyl, alkenylmethyl or alkynylmethyl of 3 to 4 carbon atoms, alkyloxyalkyl or alkylthioalkyl of 2 to 3 carbon atoms, alkanoyl or alkyl(thiocarbonyl) of 2 to 5 carbon atoms, or cyanoalkyl of 2 to 3 carbon atoms;
$R_2$ is a hydrogen atom, alkyl of 1 to 6 carbon atoms, cycloalkyl of 3 to 6 carbon atoms, alkenyl or alkynyl of 2 to 6 carbon atoms, trihalomethyl, hydroxyalkyl of 1 to 6 carbon atoms, alkyloxy or alkylthio of 2 to 6 carbon atoms, alkyloxyalkyl or alkylthioalkyl of 2 to 6 carbon atoms, pyrrolidinyl, pyrrolinyl, piperidinyl, mono- or di-alkylamino wherein each alkyl moiety contains 1 to 3 carbon atoms, halogen, cyano, nitro, or carboxyl, aryl (wherein aryl is phenyl, pyridinyl, thienyl, furanyl, pyrrolyl, imidazolyl, pyrazolyl, oxazolyl, isoxazolyl, thiazolyl or isothiazolyl) which is either unsubstituted or substituted by hydroxyl, amino, halogen, alkyl or alkyloxy of 1 to 3 carbon atoms;
$R_3$ is a hydrogen atom, methyl or halogen;
$R_4$ is a hydrogen atom, methyl, ethyl or halogen;
$R_5$ is a hydrogen atom, hydroxy, amino, hydroxymethyl or aminomethyl;
or a pharmaceutically acceptable salt thereof.

2. A compound of formula I, formula II or formula III as set forth in claim 1, wherein,
in formula I, formula II and formula III, A and D are carbon (unsubstituted or optionally substituted with methyl, cyano or halogen) or nitrogen, and B is sulfur, oxygen or nitrogen (unsubstituted or optionally substituted with methyl);
$R_1$ is methyl, ethyl, propyl, isopropyl, propenyl, propynyl, cyclopropyl, or cyclobutyl; and $R_2$ is a hydrogen atom, methyl, trihalomethyl, methoxy, pyrrolidinyl, pyrrolinyl, piperidinyl, dimethylamino, halogen, cyano, nitro or aryl (wherein aryl is phenyl, pyridinyl, thienyl, furanyl, pyrrolyl, imidazolyl, pyrazolyl, oxazolyl, isoxazolyl, thiazolyl or isothiazolyl) which is either unsubstituted or substituted by methyl, methoxy, hydroxyl, amino, or halogen;
$R_3$, $R_4$, and $R_5$ are hydrogen;
or a pharmaceutically acceptable salt thereof.

3. A compound of formula I, formula II or formula III, as set forth in claim 1, wherein,
in formula I, formula II and formula III, A, and D are carbon or nitrogen and B is sulfur oxygen or nitrogen, or
$R_1$ is ethyl or cyclopropyl;
and,
$R_2$ are hydrogen, chloro, or pyrazole;
$R_3$, $R_4$, are hydrogen;
and,
$R_5$ is hydrogen, amino or phenylethyl;
or a pharmaceutically acceptable salt thereof.

4. A compound selected from the group consisting of:
11-Ethyl-thienyl[2',3':6,5]dipyrido[2,3-b:3',2'-f]azepine;
11-Ethyl-thienyl[3',4':6,5]dipyrido[2,3-b:3',2'-f]azepine; and
2-chloro-11-Ethyl-thienyl[2',3':6,5]dipyrido[2,3-b:3',2'-f]azepine;
2-(4-pyrazolyl)-11-Ethyl-thienyl[2',3':6,5]dipyrido[2,3-b:3',2'-f]azepine;
11-Ethyl-thiazolyl[4',5':6,5]dipyrido[3,2-b:2',3'f]azepine;
11-Ethyl-oxazolyl [4',5":6,5]dipyrido[3,2-b:2',3'-e]azepine; and,
11-Ethyl-thiadiazolyl[4',5':6,5]dipyrido[3,2-b:2',3'-e]azepine;
or pharmaceutically acceptable salts thereof.

5. 2-(4-Pyrazolyl)-11-ethyl-thienyl[2',3':6,5]dipyrido[2,3-b:3',2'-f]azepine.

6. A method for preventing or treating HIV-1 infection which comprises administering, to a human being exposed to or infected by HIV-1, a prophylactically or therapeutically effective amount of a compound of formula I, formula II or formula III as set forth in claims 1, 2, 3, 4, or 5, or a pharmaceutically acceptable salt thereof.

7. A pharmaceutical composition suitable for preventing or treating HIV-1 infection which comprises a prophylactically or therapeutically effective amount of a compound of formula I, formula II or formula III, as set forth in claims 1, 2, 3, 4, or 5, or a pharmaceutically acceptable salt thereof, and a pharmaceutically acceptable carrier.

* * * * *